US010168190B2

(12) United States Patent
Lee

(10) Patent No.: US 10,168,190 B2
(45) Date of Patent: Jan. 1, 2019

(54) ELECTRONIC DEVICE AND METHOD FOR PROVIDING EXTERNAL ENVIRONMENT INFORMATION

(71) Applicant: Samsung Electronics Co., Ltd., Gyeonggi-do (KR)

(72) Inventor: Sang Hoon Lee, Gyeonggi-do (KR)

(73) Assignee: Samsung Electronics Co., Ltd. (KR)

( * ) Notice: Subject to any disclaimer, the term of this patent is extended or adjusted under 35 U.S.C. 154(b) by 472 days.

(21) Appl. No.: 14/681,732

(22) Filed: Apr. 8, 2015

(65) Prior Publication Data
US 2015/0292920 A1 Oct. 15, 2015

(30) Foreign Application Priority Data

Apr. 10, 2014 (KR) .................. 10-2014-0042948

(51) Int. Cl.
G01D 7/00 (2006.01)
G01N 33/00 (2006.01)
H04M 1/725 (2006.01)

(52) U.S. Cl.
CPC .............. *G01D 7/00* (2013.01); *G01N 33/00* (2013.01); *H04M 1/7253* (2013.01); *H04M 1/72569* (2013.01); *H04M 1/72572* (2013.01); *H04M 2250/10* (2013.01); *H04M 2250/12* (2013.01)

(58) Field of Classification Search
CPC ..... G01D 7/00; G01N 33/00; H04M 1/72572; G06F 19/3418
See application file for complete search history.

(56) References Cited

U.S. PATENT DOCUMENTS

| 8,823,520 | B2 | 9/2014 | Ly et al. |
| 9,016,565 | B2 | 4/2015 | Zhou et al. |
| 2004/0176127 | A1 | 9/2004 | Ballantyne et al. |
| 2008/0139907 | A1 | 6/2008 | Rao et al. |
| 2010/0056116 | A1* | 3/2010 | Kim .................. H04M 1/72572 455/414.1 |
| 2011/0093583 | A1 | 4/2011 | Piemonte et al. |
| 2011/0252057 | A1 | 10/2011 | Huang et al. |

(Continued)

FOREIGN PATENT DOCUMENTS

| JP | 2012220961 | 11/2012 |
| KR | 1020110122241 | 11/2011 |
| WO | WO 2011/047260 | 4/2011 |

OTHER PUBLICATIONS

European Search Report dated Sep. 24, 2015 issued in counterpart application No. 15162976.3-1972, 8 pages.

(Continued)

*Primary Examiner* — Changhyun Yi
(74) *Attorney, Agent, or Firm* — The Farrell Law Firm, P.C.

(57) ABSTRACT

A method and an electronic device for providing environment information are provided. The electronic device includes a sensor configured to measure an environmental factor and obtain first data based on the measured environmental factor, a communication module configured to receive, from at least one external electronic device, second data obtained by the at least one external device, a processor configured to generate environment information based on the first data and the received second data received, and an output module configured to display the environment information.

17 Claims, 15 Drawing Sheets

(56) References Cited

U.S. PATENT DOCUMENTS

| | | |
|---|---|---|
| 2012/0190936 A1 | 7/2012 | Rao et al. |
| 2012/0250528 A1 | 10/2012 | Yamada et al. |
| 2012/0290266 A1* | 11/2012 | Jain .................... G06F 19/3406 |
| | | 702/187 |
| 2012/0319838 A1 | 12/2012 | Ly et al. |
| 2013/0053988 A1 | 2/2013 | Lin |
| 2013/0144772 A1 | 6/2013 | Huang et al. |
| 2013/0146659 A1 | 6/2013 | Zhou et al. |
| 2013/0157729 A1 | 6/2013 | Tabe |
| 2014/0082181 A1 | 3/2014 | Piemonte |
| 2014/0143275 A1 | 5/2014 | Huang et al. |

OTHER PUBLICATIONS

International Search Report dated Jul. 16, 2015 issued in counterpart application No. PCT/KR2015/003580, 10 pages.

* cited by examiner

# ELECTRONIC DEVICE AND METHOD FOR PROVIDING EXTERNAL ENVIRONMENT INFORMATION

PRIORITY

This application claims priority under 35 U.S.C. § 119(e) to Korean patent application No. 10-2014-0042948 filed Apr. 10, 2014, the entire content of which is incorporated herein by reference.

BACKGROUND OF THE INVENTION

1. Field of the Invention

The present invention relates generally to a method and an electronic device for providing external environment information, and more particularly, to a method and electronic device for providing external environment information by using data measured in the electronic device with respect to the external environment and data received from at least one external electronic device capable of communicating with the electronic device.

2. Description of the Related Art

Typically, an electronic device only uses data measured by a measurement sensor in the electronic device, in order to provide information regarding an external environment state at a location of the electronic device to a user.

In this way, since external environment information measured by the measurement sensor embedded in a typical electronic device is provided to the user by measuring the state of the environment corresponding to a current location of the electronic device, it is difficult to check overall environment information on an area in which the electronic device is located.

Furthermore, it is difficult to provide precise environment information since the measurement sensor embedded in the typical electronic device is affected by heat and/or a magnetic field generated inside the electronic device.

SUMMARY OF THE INVENTION

The present invention is designed to address at least the problems and/or disadvantages described above and to provide at least the advantages described below.

Accordingly, an aspect of the present invention is to provide an electronic device and method for providing external environment information in order to check an area in which the electronic device is located in detail by using data measured by the electronic device and data obtained from at least one external device in which wireless communication is enabled.

Another aspect of the present invention provides an electronic device and method for providing external environment information, which enable a change history of the environment information according to movement of the electronic device to be checkable by using data obtained in the electronic device.

Another aspect of the present invention provides an electronic device and method for providing external environment information, which enable a map representing external environment information to be generated by using data obtained in the electronic device and data obtained in at least one external device.

Another aspect of the present invention provides an electronic device and method for providing external environment information, which enable an electronic device located at a first location to check environment information corresponding to a second location by receiving data obtained from external electronic devices located at the second location.

According to an aspect of the present invention, an electronic device is provided. The electronic device includes a sensor configured to measure an environmental factor and obtain first data based on the measured environmental factor; a communication module configured to receive, from at least one external electronic device, second data obtained by the at least one external electronic device; a processor configured to generate environment information based on the first data and the received second data; and an output module configured to display the environment information.

According to another aspect of the present invention, a method of providing environment information, which is performed by an electronic device, is provided. The method includes measuring an environmental factor and obtaining first data based on the measured environmental factor; receiving, from at least one external electronic device, second data obtained by the at least one external electronic device; generating environment information based on the first data and the received second data; and displaying the environment information.

According to another aspect of the present invention, a non-transitory computer readable storage medium having instructions recorded thereon, which, when executed by a computer, are able to control operations of an electronic device and allow the electronic device to perform a method. The method includes measuring an environmental factor and obtaining first data based on the measured environmental factor; receiving, from at least one external electronic device, second data obtained by the at least one external electronic device; generating environment information based on the first data and the received second data; and displaying the environment information.

BRIEF DESCRIPTION OF THE DRAWINGS

The above and other aspects, features, and advantages of certain embodiments of the present invention will be more apparent from the following detailed description taken in conjunction with the accompanying drawings, in which.

DETAILED DESCRIPTION OF EMBODIMENTS OF THE INVENTION

Figure 1:
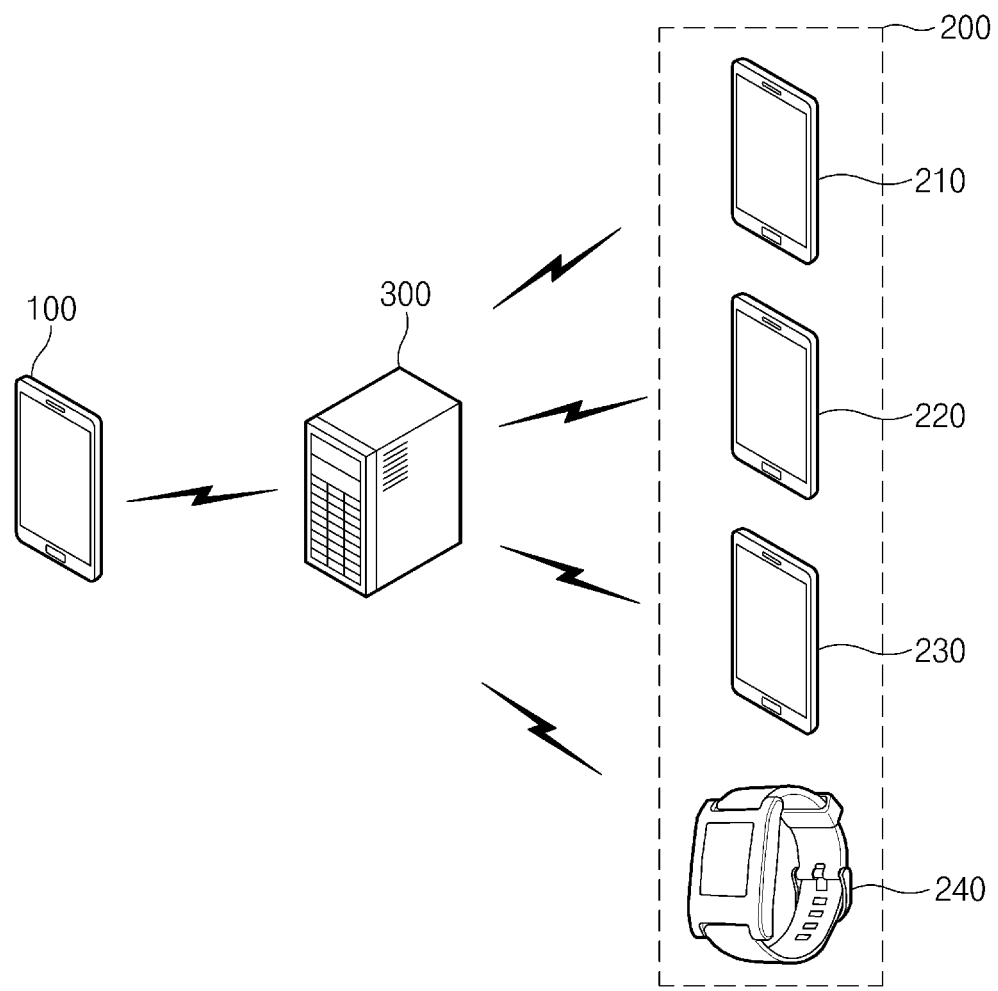
FIG. 1 is a configuration diagram illustrating a system providing external environment information according to embodiments of the present invention.

Hereinafter, various embodiments the present invention will be described with reference to the accompanying drawings. However, specific embodiments are illustrated in the drawings and detailed descriptions related thereto are provided. However, it should be understood that the particular embodiments are not intended to limit the present invention to specific forms, but rather the present invention is meant to cover all modification, equivalents, and alternatives which are included in the spirit and scope of the present invention. In the drawings, like reference numerals may refer to the same or similar elements.

The terms "include," "comprise," "including," or "comprising", as used herein, indicate functions, operations, or the existence of certain elements, but does not exclude other functions, operations or elements. The terms "comprises", "comprising,", "includes" and/or "including", when used herein, may specify the presence of stated features, integers, steps, operations, elements, and/or components, but do not preclude the presence or addition of one or more other features, integers, steps, operations, elements, components, and/or groups thereof.

The meaning of the term "or" used herein includes any combination of the words connected by the term "or". For example, the expression "A or B" or "at least one of A or/and B" may indicate A, B, or both A and B.

Terms such as "first", "second", and the like used herein may refer to various elements of various embodiments of the present invention, but do not limit the elements. For example, such terms do not limit the order and/or priority of the elements. Furthermore, such terms may be used to distinguish one element from another element. For example, "a first user device" and "a second user device" indicate different user devices. For instance, without departing the scope of the present invention, a first element may be referred to as a second element, and similarly, a second element may be referred to as a first element.

The terminology used herein is not for limiting the present invention but for describing specific embodiments. The terms of a singular form may include plural forms unless otherwise specified. As used herein, the singular forms "a," "an" and "the" are intended to include the plural forms as well, unless the context clearly indicates otherwise.

Unless otherwise defined, the terms used herein, including technical or scientific terms, have the same meanings as understood by those skilled in the art. The general terms used herein should be interpreted according to the definitions in the dictionary or in the context and should not be interpreted as an excessively contracted meaning.

Electronic devices according to embodiments of the present invention may include a communication function. For example, the electronic devices may include smart phones, tablet Personal Computers (PCs), mobile phones, Personal Digital Assistants (PDAs), Motion Picture Experts Group Audio Layer III (MP3) players, wearable devices (e.g., Head-Mounted-Devices (HMDs) such as electronic glasses), cameras, and smart watches.

Hereinafter, electronic devices according to various embodiments are described with reference to the accompanying drawings. The term "user" used herein may refer to a person who uses an electronic device or may refer to a device (e.g., an artificial electronic device) that uses an electronic device.

FIG. 1 is a configuration diagram illustrating a system providing external environment information according to embodiments of the present invention.

Referring to FIG. 1, an environment information providing system 10 includes a first electronic device 100, at least one second electronic device 200 and a provision server 300. The at least one second electronic device 200 may include devices 210, 220, and 230 that are similar or identical to the first electronic device 100, and/or a wearable device 240 interworking directly or indirectly with the first electronic device 100. However, the first electronic device 100 and the at least one second electronic device 200 may include an arbitrary electronic device performing corresponding operations to be described hereinafter.

In the following description, for convenience of explanation, the first electronic device 100 is mainly described as a master device, but may also operate as a slave device. In addition, the second electronic device 200 is mainly described as a slave device, but may also operate as a master device.

According to an embodiment of the present invention, the first electronic device 100 obtains and checks first data for external environment information. The first data may include at least one of location, altitude, illuminance, acceleration, gravity, temperature, humidity, concentration of carbon dioxide, atmospheric pressure, ultraviolet index, fine dust concentration, and radiation level. These items are provided as examples, and various items representing environment information may be additionally included. The first electronic device 100 displays the first data. The first electronic device 100 requests second data from at least one second electronic device 200 through a provision server 300. The first electronic device 100 receives, from the provision server 300, at least one second data obtained by the at least one second device 200. The second data may include at least one of location, altitude, illuminance, acceleration, gravity, temperature, humidity, concentration of carbon dioxide, atmospheric pressure, ultraviolet index, fine dust concentration, and radiation level.

According to an embodiment of the present invention, the first electronic device 100 confirms environment information on an area in which the first electronic device 100 is located. The area in which the first electronic device 100 is located may be an area within a threshold range of the location of the first electronic device 100, and the first electronic device 100 may receive the second data obtained by the second electronic device 200 located within the threshold range.

As described above, the first electronic device 100 analyzes the first data obtained in the first electronic device 100 and the second data obtained by the second electronic device 200, and check states of the first and second electronic devices 100 and 200. The first electronic device 100 checks whether there is data for which correction data needs to be generated, according to a result of checking the states of the first and second electronic devices 100 and 200. For example, the first electronic device 100 may check at least one among altitude, acceleration, and gravity included in the first and second data. The first electronic device 100 may check, from the at least checked one, the state of the first or second electronic device 100 or 200, for example, whether a user is indoors or outdoors, whether the electronic device is held in a hand of the user or is in a pocket or a bag, or whether the electronic device is located in a vehicle. The first electronic device 100 applies a respective weight or a respective priority to the first or second data according to the state of the first or second electronic device 100 or 200.

The first electronic device 100 generates correction data by applying a respective weight or a respective priority to data to which the weight or the priority needs to be applied. The first electronic device 100 may generate and output result information by using the first, second, and correction data. At this point, the result information may be average data calculated from the first, second, and correction data. The result information may be the first data measured in the first electronic device 100, when the second data is compared with the first data and is within an error range. The result information may include data corresponding to a range of the first and second data.

According to an embodiment of the present invention, the first electronic device 100 may output a map representing environment information of an area in which the first electronic device is located. The map representing the environment information may be a history information map, a group information map, and a movement route map. For example, the history information map may output a change history of the environment information checked in the first electronic device 100 that is moving. The group information map may represent environment information within a specific space in which the first electronic device is located, by grouping identical or similar data when the first and second data are identical or similar. A movement route map may represent a moving route from a location of the first electronic device 100 to a location corresponding to a keyword input in the first electronic device 100 and represent environment information on a location corresponding to the keyword.

The second electronic device 200 receives a second data request signal from the first electronic device 100 or the provision server 300 and transmits the second data to the first electronic device 100 or the provision server 300 according to the received request signal. Furthermore, the second electronic device 200 checks the state of the second electronic device 200, such as, for example, whether the user is indoors or outdoors, whether the electronic device is held in a hand of the user or is in a pocket or a bag, or whether the electronic device is located in a vehicle, and may transmit the checked result to the first electronic device 100 or the provision server 300.

When the second data request signal is received from the first electronic device 100, the provision server 300 may request the second data from the second electronic device 200 located within a threshold radius of the location of the first electronic device 100. The provision server 300 provides the second data received from the second electronic device 200 to the first electronic device 100. The provision server 300 may check a location corresponding to a keyword received from the first electronic device 100 and search for at least one second electronic device 200 existing in the location. The provision server 300 may request the second data from at least one second electronic device 200 found in the searched location. The provision server 300 may transmit map data corresponding to an area within threshold range on the basis on the location of the first electronic device 100 to the first electronic device 100. The provision server 300 may also transmit the second data obtained in the second electronic data 200, regardless of a location of the second electronic device 200, in order for the first electronic device 100 to select and use the second data as needed.

Roles of the first and second electronic devices 100 and 200 are not respectively fixed as a master and slave device, but each may dynamically function as the master and slave device. In the description herein, the first electronic device 100 is described as requesting and receiving the second data from the second electronic device 200 through communication with the provision server 300, but embodiments of the present invention are not necessarily limited hereto. For example, the first electronic device 100 may request and receive the second data through direct communication with the second electronic device 200. In addition, in the description herein, the first electronic device 100 is described as measuring environment information by using at least one of the first and second data, but embodiments of the present invention are not limited hereto. For example, the first electronic device 100 may receive the environment information from the provision server 300 and output the received environment information.

Figure 2:
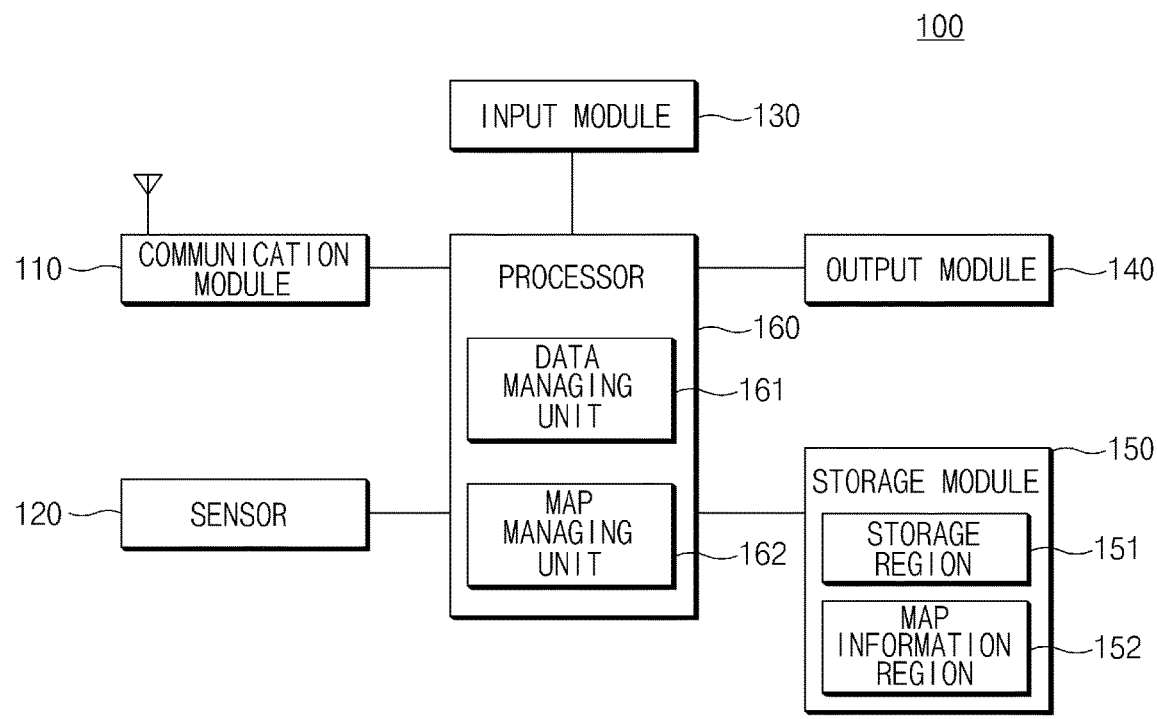
FIG. 2 is a block diagram illustrating main configuration of an electronic device providing external environment information according to embodiments of the present invention.

FIG. 2 is a block diagram illustrating a main configuration of an electronic device providing external environment information according to various embodiments of the present invention.

Referring to FIGS. 1 and 2, the first electronic device 100 includes a communication module 110, a sensor 120, an input module 130, an output module 140, a storage module 150, and a processor 160. The storage module 150 includes a storage region 151 and a map information region 152. The processor 160 includes a data managing unit 161 and a map managing unit 162.

The communication module 110 connects communications between the first electronic device 100 and an external device (e.g., the second electronic device 200 or the provision server 300). For example, the communication module 110 may communicate with the external device through wireless or wired communication. The interface for wired communication may be, for example, a Universal Serial Bus (USB), High Definition Multimedia Interface (HDMI), recommended standard (RS)-232, or Plain Old Telephone Service (POTS). The wireless communication may include, for example, at least one of Wireless Fidelity (Wi-Fi), BlueTooth (BT), Near Field Communication (NFC), Global Positioning System (GPS), or cellular communication (e.g., Long Term Evolution (LTE), LTE-Advanced (LTE-A), Code Division Multiple Access (CDMA), Wideband CDMA (WCDMA), Universal Mobile Telecommunications System (UMTS), WiBro or Global System for Mobile communications (GSM)). According to an embodiment of the present invention, the communication module 110 may request data from the external device under a control of the processor 160, and receive the requested data from the external device.

The sensor 120 includes (not shown) at least one sensor for measuring environmental factor. The sensor 120 may include a GPS sensor (not shown) for checking the location of the first electronic device 100, an altitude sensor (not shown) for checking an altitude, or a sensor for checking at least one of illuminance, acceleration, gravity, temperature, humidity, concentration of carbon dioxide, atmospheric pressure, ultraviolet index, fine dust concentration, and radiation level.

The input module 130 generates an operation signal for operating the first electronic device 100 and transmits the generated operating signal to the processor 160 according to an external input. The input module 130 may generate a signal for allowing the first electronic device 100 to obtain current environment information. The input module 130 may generate the first data checked in the first electronic device 100, a result information check signal using the second data checked in the second electronic device 200, and a check signal of a map representing environment information. The result information may include any one of average data calculated from the first and second data, the first data in case where the second data is within an error range when compared with the first data, and data corresponding to ranges of the first and second data. Furthermore, the map representing the environment information may include any one among a history information map outputting a change history of the environment information checked in the first electronic device 100 that is on the move, a group information map representing environment information within a specific space in which the first electronic device is located by grouping identical or similar data when the first and second data are identical or similar, a movement route map that may represent a moving route from a location of the first electronic device 100 to a location corresponding to a keyword input in the first electronic device 100 and represent environment information on a location corresponding to the keyword. The input module 130 may be formed of an input device such as a key button, a key pad, a touch pad, or touch screen.

The output module 140 may display an execution screen operated according to the processor 160. The output module 140 may be formed of a Liquid Crystal Display (LCD), or a touch screen etc. When formed of the touch screen, the output module 140 may display a virtual button that may generate a signal generated in the input module 130. The output module 130 may output a map representing result information calculated from the first and second data measured in the first and second electronic devices 100 and 200, and a map representing environment information.

The storage module 150 stores a program or an application for operating the first electronic device 100. The storage module 150 includes the storage region 151 for storing the first data obtained in the first electronic device 100 and the second data received from the at least one second electronic device 200. The storage module 150 stores map data for displaying the location of the first electronic device 100 and for displaying the map representing the environment information in the map information region 152.

The processor 160 generates the environment information by using the first data obtained by the sensor 120 and the second data for external environmental factor measured in the at least second electronic device 200, and outputs the environment information.

According to an embodiment of the present invention, when a signal for providing information on the external environment in which the first electronic device is located is received from the input module 130, the data managing unit 161 may obtain the first data through the sensor 120. When a signal for obtaining the second data for external environmental factor in which the second electronic device 200 is located is received from the input module, the data managing unit 161 receives the second data through the communication module 110. The first and second data include external environment information obtained in the first and second electronic devices 100 and 200, respectively. This data may be at least one of location, altitude, illuminance, acceleration, gravity, temperature, humidity, concentration of carbon dioxide, atmospheric pressure, ultraviolet index, fine dust concentration, and radiation level. The data managing unit 161 stores the obtained first and second data in the storage region 151.

According to an embodiment of the present invention, when receiving a signal for checking result information on the external environment from the input module 130, the data managing unit 161 checks the first and second data stored in the storage region 151. At this time, the second data may be data checked in the second electronic device 200 located within an arbitrary radius on the basis of a current position of the first electronic device 100. The data managing unit 161 checks states of the first and second electronic devices 100 and 200 from the first and second data and confirms whether there is data between the first and second data for which correction data needs to be generated. At this point, the processor 160 may check at least one of altitude, acceleration and gravity included in the first and second data and checks the states of the first and second electronic devices 100 and 200.

When there is data to which a respective weight or a respective priority needs to be applied between the first and second data, the data managing unit 161 generates the correction data by applying the weight or the priority to the data. The data managing unit 161 may generate result information by using the first, second and correction data. At this point, the result information may include any one of average data calculated from the first and second data, the first data in case where the second data is within an error range when compared with the first data, and data corresponding to ranges of the first and second data. The map managing unit 162 extracts map data stored in the map information region 152, include a representation of the generated result information in the map data, and output the map data to the output module 140.

According to an embodiment of the present invention, a determination of whether the weight or the priority is to be applied to at least one of the first and second data performed according to a result of checking the states of the first and second electronic devices 100 and 200, based upon the first and second data, but is not necessarily limited hereto. The data managing unit 161 may receive information notifying the state of the second electronic device 200 from the second electronic device 200 and, by using this, may check whether to apply the weight or the priority to the first or second data.

When the first electronic device 100 is exposed to the outside and the state of the second electronic device 200 is different from that of the first electronic device 100, the second data obtained in the second electronic device 200 may have lower reliability than the first data. Accordingly, correction data may be generated by applying the weight or the priority to the first data. Herein, "exposed to the outside" merely refers to outside of a smaller enclosed space, such as a bag or a clothes pocket.

According to an embodiment of the present invention, when a signal for checking a map representing external environment information from the input module 130 is received, the data managing unit 161 checks the first and second data stored in the storage region 151. The second data may be data checked by the second electronic device 200 located within an arbitrary radius on the basis of a current position of the first electronic device 100.

When the signal for checking the map representing the environment information is a signal for checking the history information map, the map managing unit 162 checks a location of the first electronic device 100 from the first data obtained by the electronic device 100 and extracts map data corresponding to the location of the first electronic device 100. The first data may include a plurality of first data items obtained at a plurality of respective locations along a movement path of the electronic device 100. The data managing unit 161 checks the change history of the first data stored in the storage region 151 and generates a movement route of the first electronic device 100 on the map data. The map managing unit displays the change history of the first data checked in the data managing unit 161 along the movement route, generates history information map of the first electronic device 100, and outputs the history information map to the output module 140. The history information map may include environment information including a plurality of environment information items based on the plurality of first data items. At this point, the history information map may display at least one of temperature altitude, illuminance, acceleration, humidity, concentration of carbon dioxide, atmospheric pressure, ultraviolet index, fine dust concentration, and radiation level.

When the signal for checking the map representing the environment information is a signal for checking a group information map, the map managing unit 162 checks the location of the first electronic device 100 from the first data obtained in the first electronic device 100 and extract map data corresponding to the location of the first electronic device 100. The data managing unit 161 confirms the second data obtained in the second electronic device 200 located within an arbitrary radius on the basis of the location of the first electronic device 100. The data managing unit 161 checks whether the first and second data are identical or similar. When the first and second data are identical or similar, the data managing unit 161 groups the first and second data, generate a group information map, and outputs the group information map to the output module 140. At this point, the group information map may display at least one altitude, illuminance, temperature, humidity, concentration of carbon dioxide, atmospheric pressure, ultraviolet index, fine dust concentration, and radiation level in a specific space in which the first electronic device 100 is located. At this point, when the first electronic device 100 is checked as located inside a building and the second electronic device is located inside the building within a threshold range from the location of the first electronic device 100 and has the same altitude as that of the first electronic device 100, the data managing unit 161 checks the second data of the second electronic device 200, and generates the group information map.

When the signal for checking the map representing the environment information is a signal for checking the movement route map, the map managing unit 162 checks the location of the first electronic device 100 from the first data obtained in the first electronic device 100 and extracts the map data corresponding to the location of the first electronic device 100. The map managing unit 162 displays the location of the first electronic device 100 on the map data and displays the first data on the location. The data managing unit 162 searches for a location corresponding to a keyword input in the input module 130. The map managing unit 162 displays a found location on the map data. The keyword may be input as a building name, a lot number address, a shop name. The data managing unit 161 checks the second data obtained in the second electronic device 200 existing at a location similar or corresponding to the keyword.

The map managing unit 162 displays a route from the location of the first electronic device 100 to the location corresponding to the keyword on the map data, displays the second data on the location corresponding to the keyword and generates the movement route map, and outputs the movement route map via the output module 140. The movement route map displays the location of the first electronic device 100 and at least one of altitude, illuminance, temperature, humidity, concentration of carbon dioxide, atmospheric pressure, ultraviolet index, fine dust concentration, and radiation level at the location corresponding to the keyword.

According to an embodiment of the present invention, the data managing unit 161 outputs a warning message for the environment information through a message popup window. For example, when the ultraviolet index is at least a threshold value, a message for moving to avoid the ultraviolet rays is output. When a room temperature is less than an outdoor temperature by at least a threshold value, a message for raising the room temperature is output.

The electronic device 100 according to an embodiment of the present invention includes the sensor 120 measuring environmental factor and obtaining the first data, the communication module 110 communicating with at least one external electronic device, the processor 160 generating environment information by using the first data and the second data received in the external electronic device, and the output module 140 displaying the environment information.

According to an embodiment of the present invention, the environmental factor includes at least one of temperature, humidity, concentration of carbon dioxide, atmospheric pressure, and an ultraviolet index.

According to an embodiment of the present invention, the at least one external electronic device is located within a threshold range from the electronic device.

According to various embodiments of the present invention, the generation of the environment information includes applying a respective weight or a respective priority to at least one of the first and second data.

According to various embodiments of the present invention, the processor 160 checks a state of each electronic device in the first and second data and checks whether the weight or the priority is applied.

According to various embodiments of the present invention, the first data includes a plurality of first data items obtained at a plurality of respective locations along a movement path of the electronic device, the environment information includes a plurality of environment information items based on the plurality of first data items, the processor 160 generates a history information map including the environment information, and, the output module 140 displays the history information map.

According to various embodiments of the present invention, the processor 160 generates, when the first and second data are within a predetermined range each other, a group information map by grouping the first and second data together, and the output module 140 displays the group information map.

According to various embodiments of the present invention, the processor 160 checks the second data obtained by the at least one external electronic device at a location corresponding to an input keyword and generates a movement route map including a route from a location a location of the electronic device to a location corresponding to the keyword, and the output module 140 displays the movement route map.

According to various embodiments of the present invention, the second data is generated based on an environmental factor measured by the at least one external electronic device.

Figure 3:
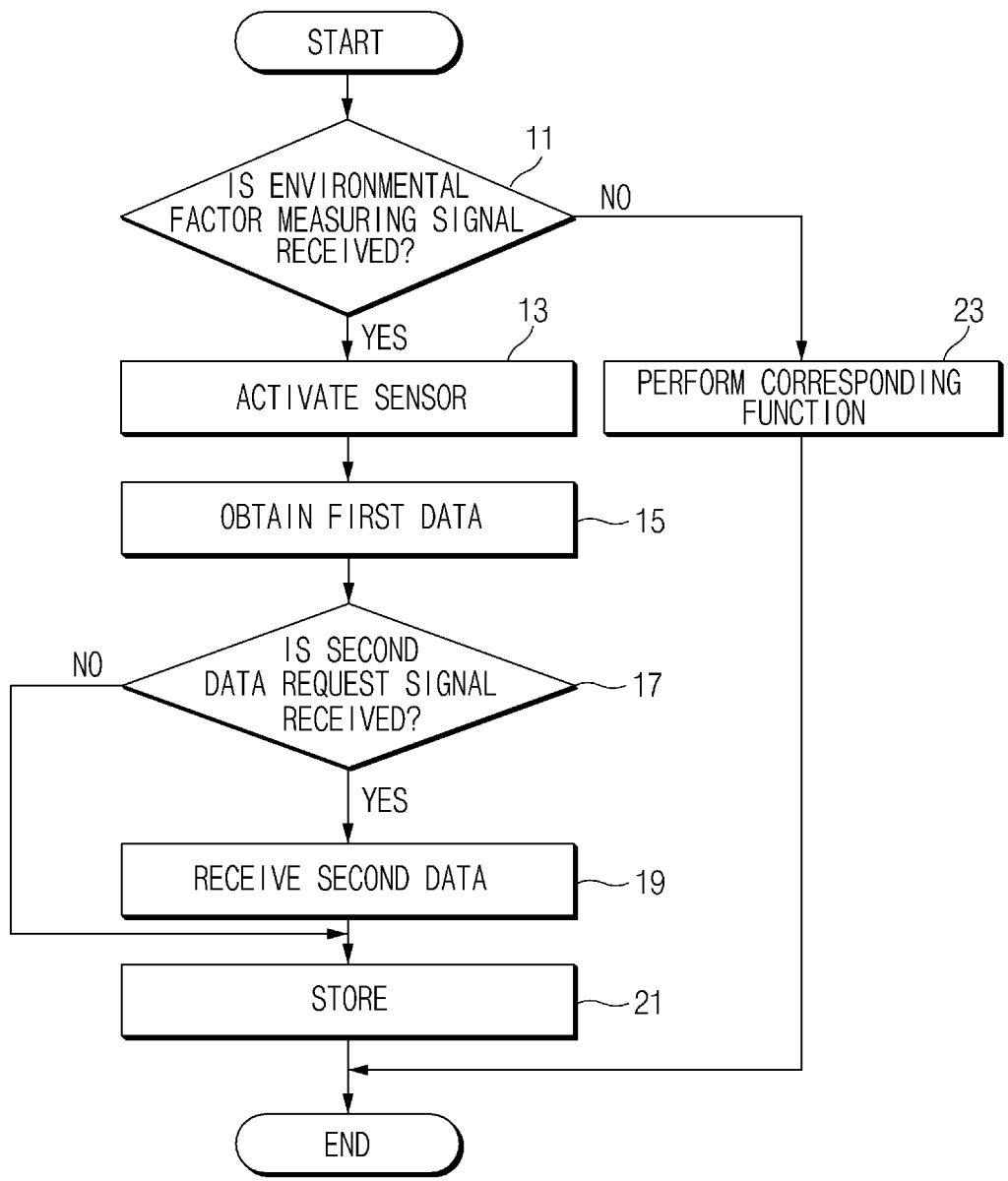
FIG. 3 is a flowchart illustrating a method that an electronic device obtains first and second data according to embodiments of the present invention.

FIG. 3 is a flowchart illustrating a method of obtaining, by an electronic device, first and second data according to various embodiments of the present invention.

Referring to FIGS. 1 to 3, in step 11, when a signal for measuring an environmental factor in which the first electronic device 100 is located is received from the input module 130, the processor 160 of the first electronic device 100 activates the sensor 120 in step 13. In step 11, when the signal is not received, the processor 160 continuously performs a corresponding function in step 23. The external environment information may be at least one of location, altitude, illuminance, acceleration, gravity, temperature, humidity, concentration of carbon dioxide, atmospheric pressure, ultraviolet index, fine dust concentration, and radiation level.

In step 15, the processor 160 obtains the first data. The first data may be environment information containing measurements of the external environmental factor of the first electronic device 100. In step 17, when a request signal for the second data is received, the processor 160 receives the second data from the second electronic device 200, in step 19. When the request signal is not received, the processor 160 stores the obtained first data in step 21.

In performing steps 17 through 19, the processor 160 may transmit a request signal for the second data through direct communication with the second electronic device 200, and receive the second data from the second electronic device 200. In various embodiments of the present invention, the processor 160 may request the second data from the provision server 300. When the first electronic device 100 requests the second data from the provision server 300, the provision server 300 transmits, to the first electronic device, the second data received from the second electronic device 200 and stored by the provision server 300. In step 21, the processor 160 stores the obtained first data and the second data in the storage module 150.

Figure 4:
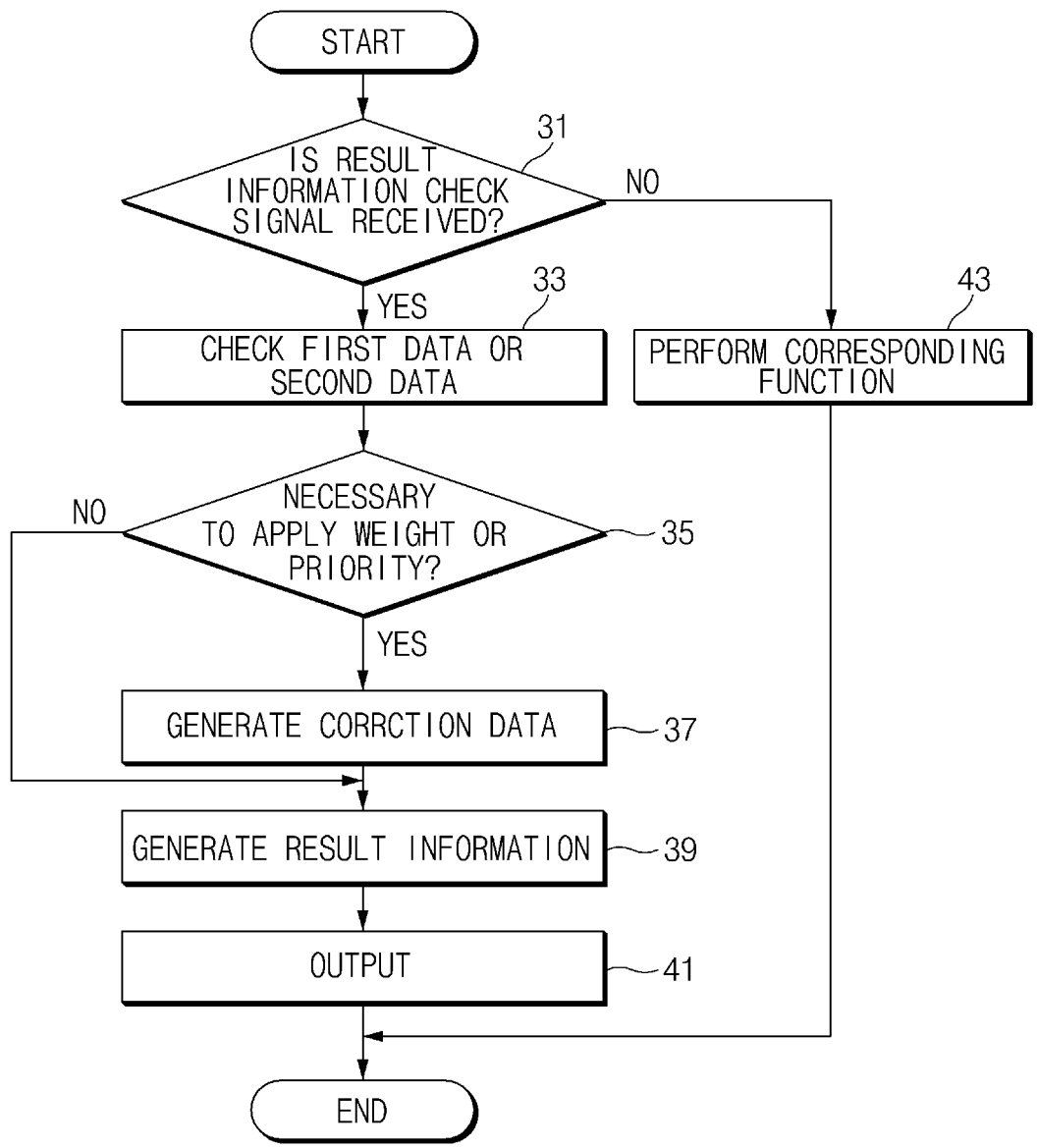
FIG. 4 is a flowchart illustrating a method of providing environment information on an area in which an electronic device is located according to embodiments of the present invention.

FIG. 4 is a flowchart illustrating a method of providing environment information on an area in which an electronic device is located according to various embodiments of the present invention.

Referring to FIGS. 1 to 4, in step 31, when a signal for checking result information on external environment is received from the input module 130, in step 33, the processor 160 checks the first and second data stored in the storage module 150, such as in step 21 of FIG. 3. In step 31, when the signal is not received, the processor 160 continuously performs a corresponding function, in step 43.

The second data may be data checked in the second electronic device 200 located within an arbitrary radius on the basis of a current location of the first electronic device 100. In step 35, the processor 160 checks whether there is data for which correction data needs to be generated (e.g., application of the weight or the priority is necessary) between the confirmed first and second data. The processor 160 may confirm the state of the first electronic device 100 from the first data and the state of the second electronic device 200 from the second data.

When it is determined that there is data between the first and second data to which the weight or the priority is necessary to be applied in step 35, the processor 160 generates correction data by applying the weight or the priority to data to which the weight or the priority needs to be applied, in step 37. When it is determined that there is no data between the first and second data to which the weight or the priority is necessary to be applied in step 35, the processor 160 the processor 160 generates result information by using the first and second data, and the correction data, in step 39. The processor 160 may check at least one piece of information on luminance, acceleration, and gravity included in the first and second data. The processor 160 may check at least one piece of information on luminance, acceleration, and gravity included in the first and second data. The processor 160 may check a state of the first or second electronic device 100 or 200, for example, whether the user is indoors or outdoors, whether an electronic device is held in a hand of the user or in a pocket or a bag, or whether an electronic device is in a vehicle from the at least one piece of information. According to an embodiment of the present invention, a determination of whether the weight or the priority is applied is described as confirmed based upon the first and second data, but embodiments of the present invention are not limited hereto. Information notifying the state of the second electronic device 200 may be received from the second electronic device 200. In step 39, the processor 160 may generate the result information by using the first and second data and perform step 41.

In step 41, the processor 160 outputs the calculated result information to the output module 140. According to an embodiment of the present invention, the first and second electronic devices 100 and 200 are both present in an identical space A, the first electronic device 100 obtains the first data for an external environmental factor at a specific location within the A space and the second electronic device 200 may obtain the second data at a specific location (e.g., a location different from the location of the first electronic device 100). The processor 160 generates the result information on the first and second data. Before the result information is calculated, when the state of the second electronic device 200 is different from the state of the first electronic device 100, which is exposed to outside, reliability of the second data obtained in the second electronic device 200 is slightly lower than that of the first electronic device 100, and thus the correction data is generated by applying the weight or the priority to the first data. Accordingly, the processor 160 accurately checks environment information within the space A.

Figure 5:
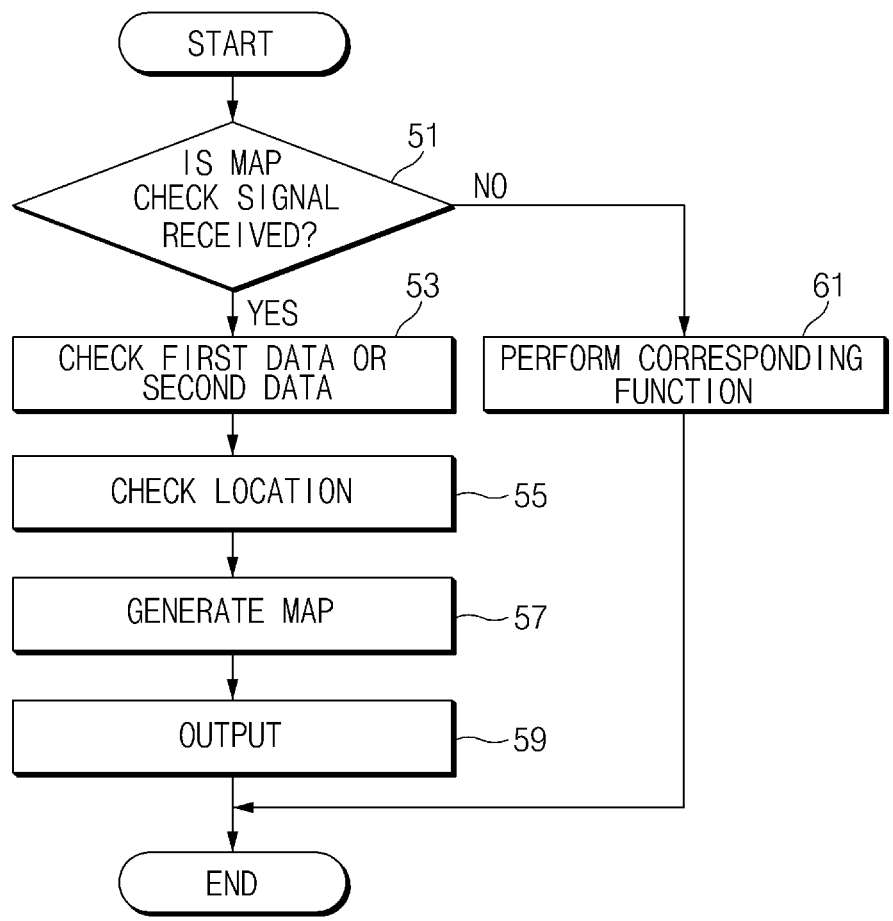
FIG. 5 is a flowchart illustrating a method of providing a map that an electronic device is able to represent environment information according to embodiments of the present invention.

FIG. 5 is a flowchart illustrating a method of providing a map on which an electronic device is able to represent environment information according to an embodiment of the present invention.

Referring to FIGS. 1 to 3 and FIG. 5, in step 51, when a signal for checking result information on external environment is received from the input module 130, the processor 160 checks the first data or the second data stored in the storage module 150, such as in step 21 in FIG. 3. In step 51, when the signal for checking the result information is not received, the processor 160 performs continuously performs a corresponding function, in step 61.

In step 55, the processor 160 checks the location of the first electronic device 100 from the first data. When the second data is checked in step 53, the processor 160 checks the location of the second electronic device 200 from the second data in step 55. In step 57, the processor 160 generates the map for the first or second data and outputs the generated map to the output module 140 in step 59.

According to an embodiment of the present invention, the processor 160 may check the location of the first electronic device 100 from the first data obtained by the first electronic device 100 and receive map data corresponding to the location of the first electronic device 100 from the provision server 300. The processor 160 may generate a movement route of the first electronic device 100 on the map data. The processor 160 may display the first data along the generated movement route and generate a history information map of the first electronic device 100. At this point, the history information map may display at least one of temperature, altitude, illuminance, acceleration, humidity, concentration of carbon dioxide, atmospheric pressure, ultraviolet index, fine dust concentration, and radiation level along the movement route.

According to an embodiment of the present invention, the processor 160 may confirm the location of the first electronic device 100 from the first data obtained from the first electronic device 100 and receive the map data corresponding to the location of the first electronic device 100 from the provision server 300. When the first electronic device 100 is located inside a building, the processor 160 may check an altitude from the first data. The processor 160 may check the second data obtained by the second electronic device 200 located within an arbitrary radius on the basis of the location of the first electronic device 100. The processor 160 may check that the first and second data are identical or similar. When the first and second data are identical or similar, the processor 160 may generate a group information map by grouping locations checked in the first and second data. At this point, the group information map may display at least one of altitude, illuminance, temperature, humidity, concentration of carbon dioxide, atmospheric pressure, ultraviolet index, fine dust concentration, and radiation level within a specific space in which the first electronic device 100 is located.

According to an embodiment of the present invention, the processor 160 may check the location of the first electronic device 100 from the first data obtained by the first electronic device and receive map data corresponding to the location of the first electronic device 100 from the provision server 300. The processor 160 may display the location of the first electronic device 100 and the first data on the location. The processor 160 may display the location corresponding to a keyword input from the input module 130 on the map data. The keyword may be input as a building name, a lot number address, or a shop name, for example. The processor 160 may check the second data obtained in the second electronic device 200 existing at a location corresponding to the keyword or a similar location. The processor 160 may display a route from a current location to a location corresponding to the keyword on the map data, and generate a movement route map by displaying the second data on a location corresponding to the keyword. At this point, the movement route map may display at least one of altitudes, illuminances, temperatures, humidities, concentration of carbon dioxide, atmospheric pressure, ultraviolet index, fine dust concentrations, and radiation levels of the location of the first electronic device 100 and the location corresponding to the keyword.

According to an embodiment of the present invention, a method in which an electronic device 100 provides environment information may include an operation of measuring external environmental factor and creating first data based on the measured environmental factor, an operation of receiving, from at least one external electronic device, second data obtained by the at least one external device, an operation of generating environment information based on the first data and the received second data, and an operation of displaying the environment information.

According to an embodiment of the present invention, the environmental factor includes at least one of temperature, humidity, concentration of carbon dioxide, atmospheric pressure, and an ultraviolet index.

According to an embodiment of the present invention, the at least one external electronic device is located within a threshold range from the electronic device.

According to an embodiment of the present invention, generating the environment information includes applying a respective weight or a respective priority to at least one of the first and second data.

According to an embodiment of the present invention, the method further includes an operation of checking a state of each of the electronic device and the at least one external electronic device based upon the first and second data; and an operation of determining whether the weight or the priority is applied according to a result of checking the state of each of the electronic device and the at least one external electronic device.

According to an embodiment of the present invention, measuring the environmental factor and obtaining the first data based on the environmental factor includes obtaining a plurality of first data elements at a plurality of respective locations along a movement path of the electronic device, wherein generating the environment information includes generating a plurality of environment information items based on the plurality of first data items, and the method further includes an operation of generating a history information map including the plurality of environmental information items; and an operation of displaying the history information map.

According to an embodiment of the present invention, the method further includes an operation of generating a group information map by grouping the first and second data when the first and second data are within a predetermined range each other; and an operation of displaying the group information map.

According to an embodiment of the present invention, the method further includes an operation of generating a route map including a route from a location of the electronic device to a location corresponding to an input keyword and further including environment information of the location corresponding to the input keyword; and an operation of displaying the route map.

According to an embodiment of the present invention, the second data is generated based on an environmental factor measured by the at least one external electronic device.

Figure 6A:
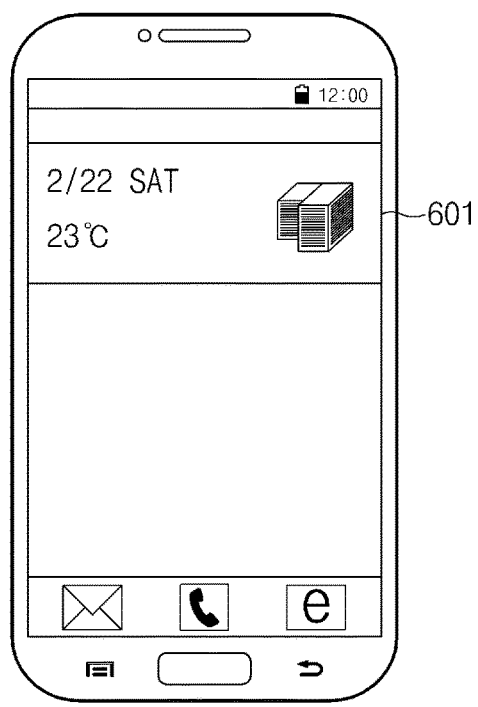
FIGS. 6A to 6C are screen views illustrating provision of environment information on an area in which an electronic device is located according to embodiments of the present invention.
Figure 6B:
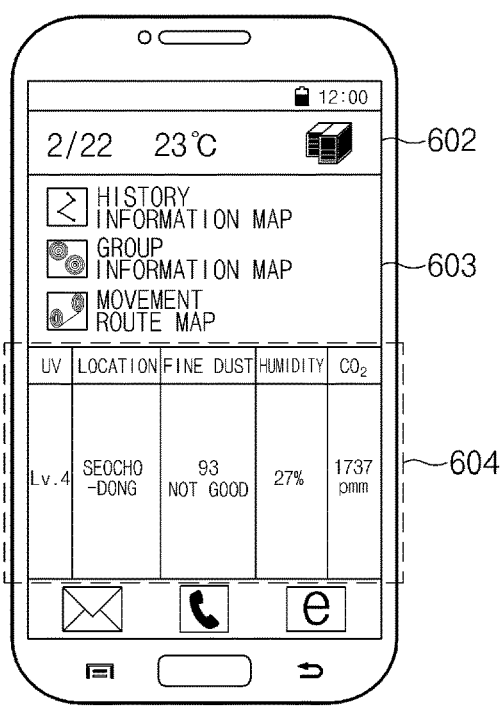
Figure 6C:
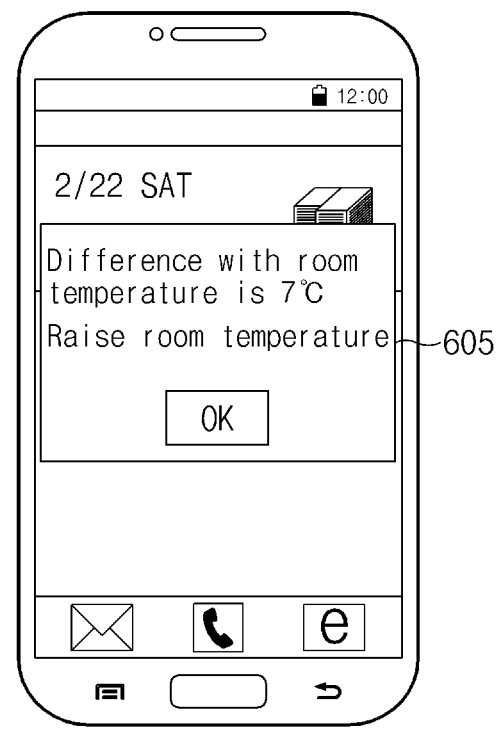

FIGS. 6A to 6C are screen views illustrating provision of environment information on an area in which an electronic device is located according to various embodiments of the present invention.

Referring FIGS. 2 and 6, the first electronic device 100 displays environment information regarding a place at which the first electronic device 100 is located in a widget-type display area on an idle screen, as shown in reference numeral 601 of FIG. 6A. The user is able to check today's date and day, a current temperature, or a fact that the first electronic device 100 is located indoors, etc. The temperature written in reference numeral 601 may be an average temperature calculated by using temperatures checked from the first and second data.

When the user selects reference numeral 601 of FIG. 6A, the first electronic device 100 displays a screen as shown in FIG. 6B. The first electronic device 100 displays content shown in reference numeral 601 as in FIG. 6B, and displays a screen for selecting a kind of a map for checking a map for environment information as in reference numeral 603. The history information map may be a menu for checking a change history of environment information checked by the first electronic device 100, which is moving. The group information map may be a menu for grouping identical or similar data when the first and second data are identical or similar and checking a map representing environment information within a specific space in which the first electronic device is located. The movement route map may be a menu for displaying a movement route from the location of the first electronic device 100 to the location corresponding to the keyword input in the first electronic device 100 and checking a map representing environment information on the location corresponding to the keyword. Reference numeral 604 indicates result information calculated from the first data obtained in the first electronic device 100 and the second data obtained in the second electronic device 200 existing within a threshold range on the basis of the location of the first electronic device 100.

According to an embodiment of the present invention, when the first electronic device 100 is indoors as checked in FIG. 6A, and a temperature at a place where the first electronic device 100 is located and an external temperature are differed by a threshold value or greater, a message popup window is output, as shown in reference numeral 605 of FIG. 6C. By providing the message popup window to the user in order that an indoor and outdoor temperature difference is properly maintained, energy usage is reduced.

Figure 7A:
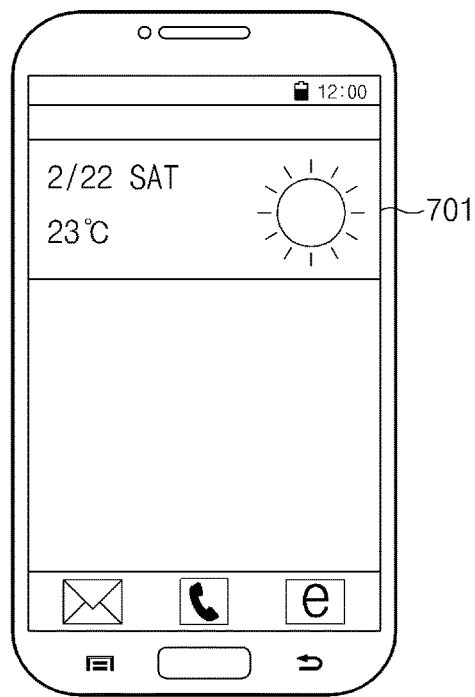
FIGS. 7A to 7C are screen views illustrating provision of a history information map in which a history of environment information is representable according to movement of an electronic device according to embodiments of the present invention.
Figure 7B:
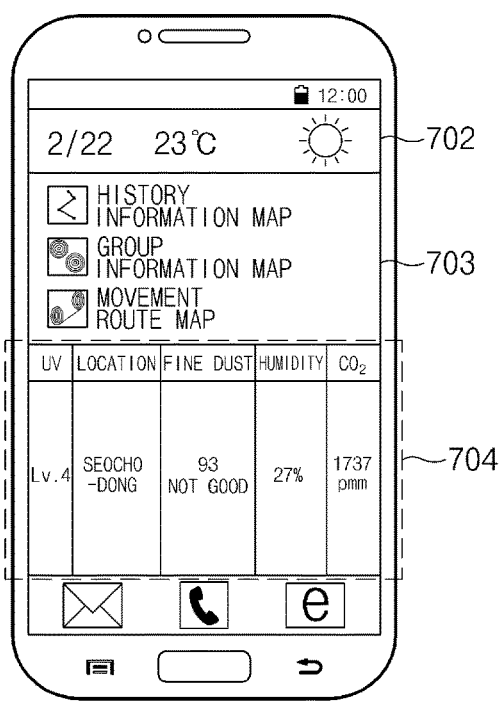
Figure 7C:
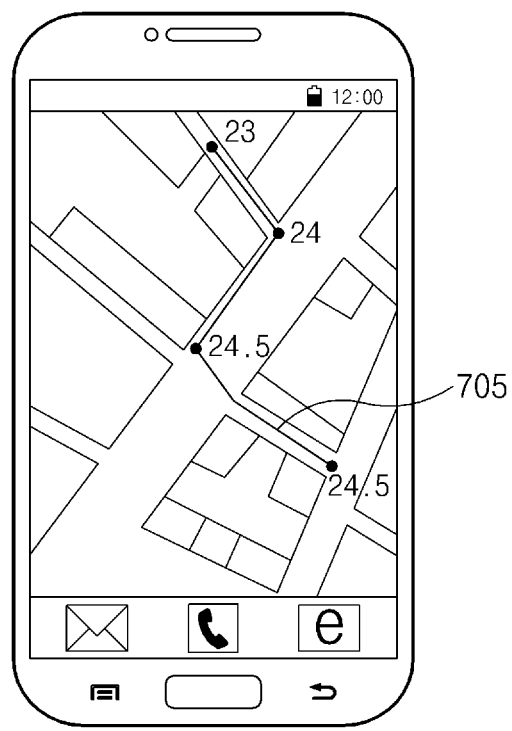

FIGS. 7A to 7C are screen views illustrating provision of history map representing environment information history according to movement of an electronic device according to various embodiments of the present invention.

Referring to FIGS. 1, 2, 6A to 6C and 7A to 7Cc, the first electronic device 100 displays environment information regarding a location of the first electronic device 100 in a widget-type display area on an idle screen as in a reference numeral 701 of FIG. 7A. The user is able to check today's date and day, a current temperature, or an indication that the first electronic device 100 is located outdoors, etc. A temperature written in reference numeral 701 may be an average temperature calculated by using temperatures checked from the first and second data.

When the user selects reference numeral 701 of FIG. 7A, the first electronic device 100 displays a screen as shown in FIG. 7B. The first electronic device 100 displays content shown in reference numeral 701 of FIG. 7B, and display a screen for selecting a kind of map for checking a map for environment information as in reference numeral 703. The kind of map is similar to that described herein with reference to FIGS. 6A to 6C. Reference numeral 704 indicates result information calculated from the first data obtained in the first electronic device 100 and the second data obtained in the second electronic device 200 existing within a threshold range on the basis of the location of the first electronic device 100.

According to an embodiment of the present invention, when a signal for selecting a history information map among those shown in a reference numeral 703 of FIG. 7B is input, the first electronic device 100 displays a movement route of the first electronic device 100, such as shown in reference numeral 705 of FIG. 7C and the first data measured at each specific interval. For example, the first electronic device 100 may check the location of the first electronic device 100 from the first data obtained from the first electronic device 100 and receive map data corresponding to the location of the first electronic device 100 from the provision server 300. The first electronic device 100 may generate the movement route of the first electronic device 100 on the map data. The first electronic device 100 may display the first data along the generated movement route, generate and display a history information map of the first electronic device 100. The history information map may display at least one of temperature, altitude, illuminance, acceleration, temperature, humidity, concentration of carbon dioxide, atmospheric pressure, ultraviolet index, fine dust concentration, and radiation level according to the movement route.

Figure 8A:
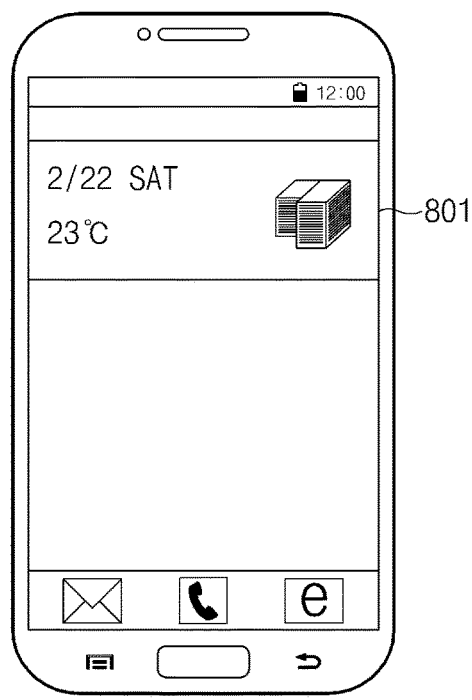
FIGS. 8A to 8C are screen views illustrating of a group information map representing environment information on a specific area in which an electronic device is located according to embodiments of the present invention.
Figure 8B:
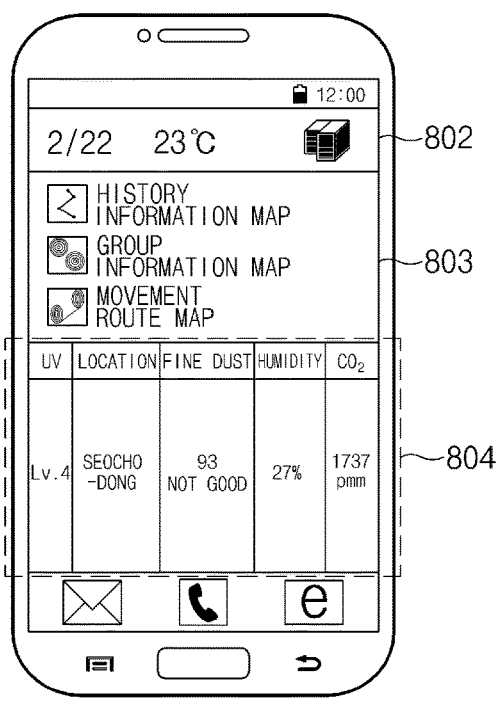
Figure 8C:
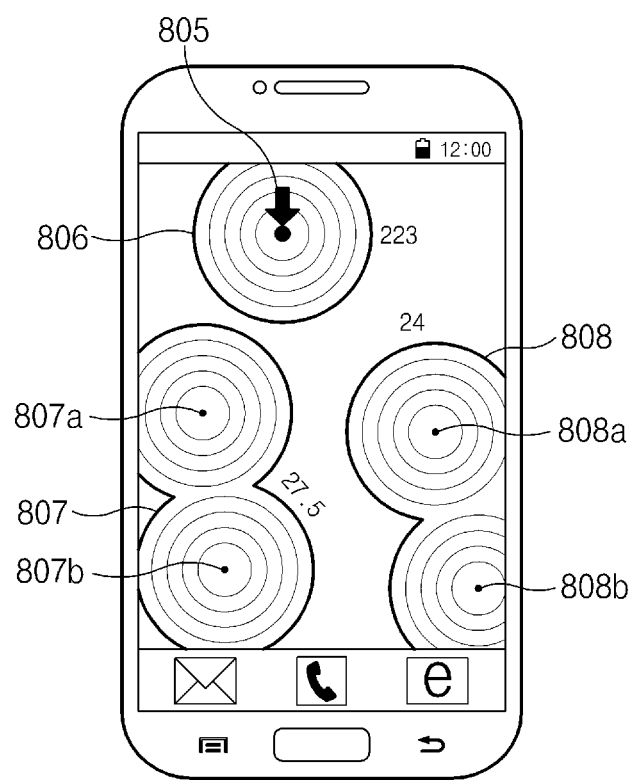

FIGS. 8A to 8C are screen views illustrating provision of a group information map representing environment information on a specific area in which an electronic device is located according to various embodiments of the present invention.

Referring to FIGS. 1, 2, 6A to 6C, and 8A to 8C, the first electronic device 100 displays environment information regarding a location of the first electronic device 100 in a widget-type display area on an idle screen, as shown at reference numeral 801 of FIG. 8A. Certain features of FIGS. 8A and 8B are similar to corresponding features described herein with respect to FIGS. 6A and 6B, and are therefore omitted.

According to an embodiment of the present invention, when a signal is input for selecting a group information map among those shown in a reference numeral 803 of FIG. 8B, the first electronic device 100 displays the group information map within a threshold range on the basis of the location of the first electronic device 100, as shown in FIG. 8C. For example, the first electronic device 100 may check the location of the first electronic device 100 from the first data obtained from the first electronic device 100 and receive map data corresponding to the location of the first electronic device 100 from the provision server 300. The first electronic device 100 may display the location of the first electronic device 100 within a specific area in which the first electronic device is located like a reference numeral 805. The first electronic device 100 may group data having identical or similar data in the specific area like a reference numeral 806. The first electronic device 100 may check and display the location of the second electronic device 200 like reference numerals 807a, 807b, 808a, and 808b. The first electronic device 100 may confirm identical or similar data among the first and second data. The first electronic device 100 may group the identical or similar data, generate and display the group information map.

For example, when temperatures obtained by the second electronic device 200 and corresponding to reference numerals 807a and 807b are identical as 27.5□, the first electronic device 100 generates the second data checked in the second electronic device 200 and corresponding to the reference numerals 807a and 807b as one group, such as shown at reference numeral 807. In addition, temperatures obtained in the second electronic device 200 and corresponding to reference numerals 808a and 808b are identical as 24□, the first electronic device 100 generates the second data checked in the second electronic device 200 and corresponding to the reference numerals 808a and 808b as one group like a reference numeral 808. At this point, the group information map may display at least one of altitude, illuminance, temperature, humidity, concentration of carbon dioxide, atmospheric pressure, ultraviolet index, fine dust concentration, and radiation level in a specific space in which the first electronic device 100 is located. When the first electronic device 100 is checked as located inside a building, the second data is checked for the second electronic device 200 located within a threshold range from the location of the first electronic device 100 and having the same altitude as that of the first electronic device 100, and the group information map is generated and displayed.

FIGS. 9A to 9E are screen views illustrating provision of a movement route map representing state information on a location set by an electronic device according to various embodiments of the present invention.

Figure 9A:
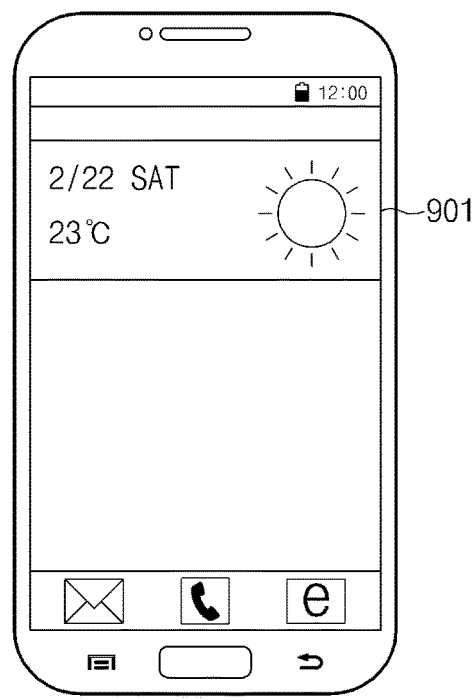
FIGS. 9A to 9E are screen views illustrating provision of a movement route map representing state information on a location set by an electronic device according to embodiments of the present invention.
Figure 9B:
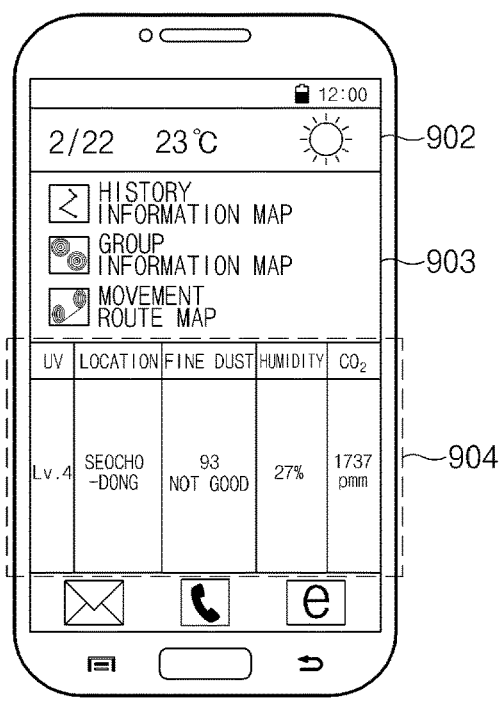

Referring to FIGS. 1, 2, 7A to 7C, and 9A to 9E, the first electronic device 100 displays environment information regarding a location of the first electronic device 100 in a widget-type display area on an idle screen as in a reference numeral 901 of FIG. 9A. Detailed descriptions of certain features of FIGS. 9A and 9B are similar to corresponding features described herein with respect to FIGS. 7A and 7B, and are therefore omitted.

Figure 9C:
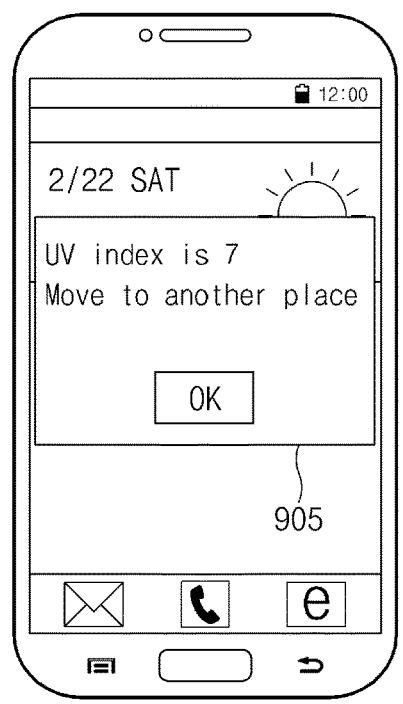

According to an embodiment of the present invention, when a signal is input for selecting a movement route map among those shown in a reference numeral 903 of FIG. 9B, the first electronic device 100 displays the movement route map within a threshold range on the basis of the location of the first electronic device 100, as shown in FIG. 9C. For example, when the ultraviolet index checked from the first data at least equal to a threshold value, the first electronic device 100 notifies a user of the ultraviolet index, such as at reference numeral 905 of FIG. 9C and displays a message popup window for recommending movement to another place. The threshold value of the ultraviolet index displayed on the message popup window may be set by the user. In addition, the output message popup window is not limited to messages regarding UV rays, but may be output for at least one of environment information included in the first data, such as fine dust concentration, humidity, and concentration of carbon dioxide.

Figure 9D:
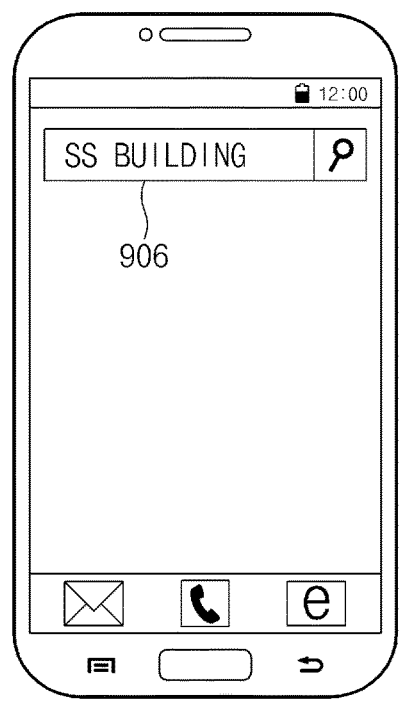
Figure 9E:
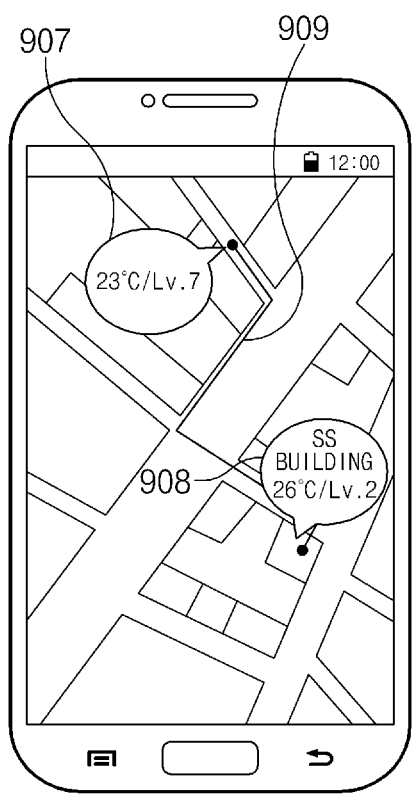

As shown at reference numeral 905 of FIG. 9C, when a "check" area is selected, the first electronic device 100 displays a screen, such as shown in FIG. 9D. When a user inputs a keyword to an input field at reference numeral 906 of FIG. 9D, the first electronic device 100 checks a location corresponding to the input keyword. According to an embodiment of the present invention, the first electronic device 100 checks the location of the first electronic device 100 from the first data obtained in the first electronic device 100 and receives map data corresponding to the location of the first electronic device 100 from the provision server 300. The first electronic device 100 displays the location of the first electronic device 100 and displays the first data on the location, such as shown at reference numeral 907.

The first electronic device 100 may display a location corresponding to the keyword input from the user on the map data. At this point, the keyword may be input as a building name, a lot number address, a shop name. The first electronic device 100 may check the second data obtained by the second electronic device 200 existing at a location corresponding to the keyword or at a similar location. The first electronic device 100 displays a route from a current location to a location corresponding to the keyword on the map data, such as shown at reference numeral 909, displays the second data at the location corresponding to the keyword, such as shown at reference numeral 908, and generates and displays the movement route map. The movement route map may display at least one of altitudes, illuminances, temperatures, humidities, concentrations of carbon dioxide, atmospheric pressures, ultraviolet indexes, fine dust concentrations, and radiation levels of the location of the first electronic device 100 and the location corresponding to the keyword. In response to a user input in a state where a screen FIG. 9C is not displayed, the first electronic device 100 may display a screen of FIG. 9D.

Figure 10:
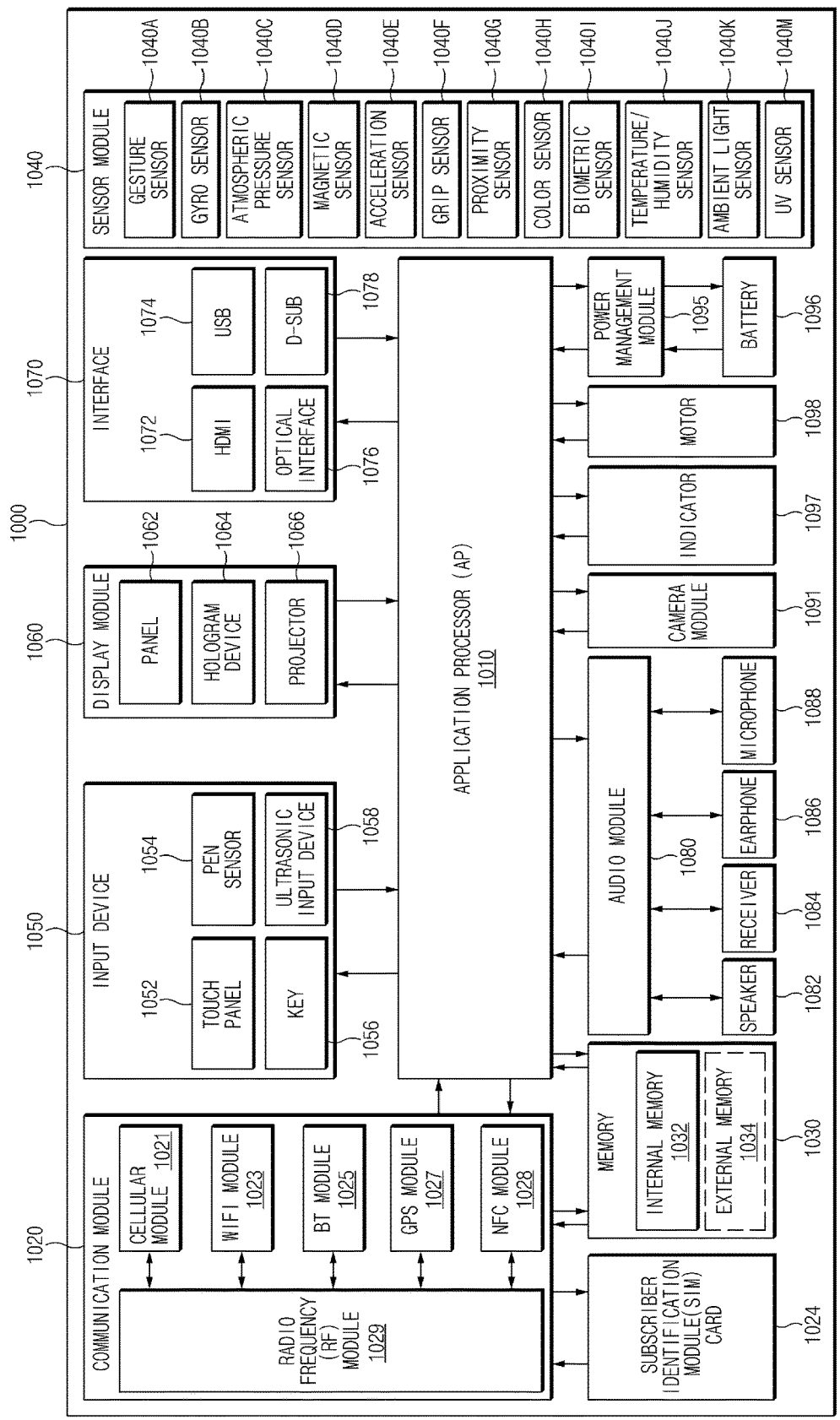
FIG. 10 is a block diagram illustrating an electronic device according to embodiments of the present invention.

FIG. 10 is a block diagram illustrating an electronic device according to an embodiment of the present invention.

Referring to FIG. 10, an electronic device 1000 according to the present invention configures, at least a portion of the electronic device 100 illustrated in FIG. 2.

Referring FIG. 10, the electronic device 1000 includes at least one Application Processor (AP) 1010, a communication module 1020, a Subscriber Identification Module (SIM) card 1024, a memory 1030, a sensor 1040, an input device 1050, a display 1060, an interface 1070, an audio module 1080, a camera module 1091, a power management module 1095, a battery 1096, an indicator 1097, or a motor 1098.

The AP 1010 (such as the processor 160 shown in FIG. 2, for example) may drive an operating system or an application program and control a plurality of hardware or software elements connected thereto, and perform various data processing and operations including multimedia data. The AP 1010 may be implemented with, for example, System on a Chip (SoC). According to an embodiment of the present invention, the AP 1010 may further include a Graphics Processing Unit (GPU, not shown).

The communication module 1020, for example, the communication module 110 performs data transmission and reception in communication between the electronic device 1000 (e.g., the electronic device 100) and other electronic devices connected through a network. According to an embodiment of the present invention, the communication module 1020 includes a cellular module 1021, a Wi-Fi module 1023, a BT module 1025, a GPS module 1027, an NFC module 1028, and a Radio Frequency (RF) module 1029.

The cellular module 1021 provides a voice call, a video call, a text messaging service, or an internet service, etc., through a communication network (e.g., LTE, LTE-A, CDMA, WCDMA, UMTS, WiBro, or GSM, etc.). In addition, the cellular module 1021 may identify or authenticate an electronic device in a communication network by using, for example, a Subscriber Identification Module (e.g., the SIM card 1024). According to an embodiment of the present invention, the cellular module 1021 may perform at least a portion of functions enabled by the AP 1010. For example, the cellular module 1021 may perform at least a portion of multimedia control function.

According to an embodiment of the present invention, the cellular module 1021 may include a Communication Processor (CP) (not shown). In addition, the cellular module 1021 may be implemented with, for example, an SoC. Although, in FIG. 10, elements such as the cellular module 1021 (e.g., a CP), the memory 1030, and the power management module 1095 are illustrated as separate from the AP 1010, according to embodiments of the present invention, the AP 1010 may be implemented to include at least some of these above-described elements (e.g., the cellular module 1021).

According to an embodiment of the present invention, the AP 1010 or the cellular module 1021 (e.g., CP) may load, on a volatile memory, commands or data received from at least one of a nonvolatile memory and other elements and process them. Furthermore, the AP 1010 or the cellular module 1021 may store, in the nonvolatile memory, data received from or generated by at least one of other elements.

The Wi-Fi module 1023, the BT module 1025, the GPS module 1027 or the NFC module 1028 may each respectively include, for example, a processor for processing data transmitted or received through the corresponding module. Although, in FIG. 10, the cellular module 1021, the Wi-Fi module 1023, the BT module 1025, the GPS module 1027 or the NFC module 1028 are illustrated as separate blocks, according to an embodiment of the present invention, two or more of these elements may be included in a single Integrated Chip (IC) or an IC package. For example, two or more (e.g., a CP corresponding to the cellular module 1021 and a Wi-Fi processor corresponding to the Wi-Fi module) of processors respectively corresponding to the cellular module 1021, the Wi-Fi module 1023, the BT module 1025, the GPS module 1027 or the NFC module 1028 may be implemented as one SoC.

The RF module 1029 transmits and receives data, for example, an RF signal. Although not shown in FIG. 10, the RF module 1029 may include, for example, a transceiver, a Power Amp Module (PAM), a frequency filter, or a Low Noise Amplifier (LNA), etc. In addition, the RF module 1029 may further include components, for example, a conductor or a wire for transmitting and receiving an electromagnetic wave in a free space in a wireless communication. In FIG. 10, although the cellular module 1021, the Wi-Fi module 1023, the BT module 1025, the GPS module 1027 and the NFC module 1028 are illustrated as sharing one RF module 1029, according to an embodiment of the present invention, at least one of the cellular module 1021, the Wi-Fi module 1023, the BT module 1025, the GPS module 1027 and the NFC module 1028 may transmit and receive an RF signal through a separate RF module.

The SIM card 1024 may be inserted into a slot formed at a specific position of the electronic device. According to various embodiments of the present invention, the SIM card 1024 may be embedded in the electronic device in a chip type or stored in a portion (e.g., an electronic SIM, virtual SIM, or soft SIM) of the corresponding electronic device without any physical form. The SIM card 1024 may include unique identification information (e.g., an Integrated Circuit Card IDentifier (ICCID)) or subscriber information (e.g., an International Mobile Subscriber Identity (IMSI)).

The memory 1030, for example, the storage module 150 shown in FIG. 2, may include an internal memory 1032 or an external memory 1034. The internal memory 1032 includes at least one of, for example, a volatile memory (e.g., a Dynamic RAM (DRAM), Static RAM (SRAM), Synchronous Dynamic RAM (SDRAM) etc.) or a nonvolatile memory (e.g., a One Time Programmable ROM (OTROM), Programmable ROM (PROM), Erasable and Programmable ROM (EPROM), Electrically Erasable and Programmable ROM (EEPROM), mask ROM, flash ROM, NAND flash memory, NOR flash memory, etc.).

According to an embodiment of the present invention, the internal memory 1032 may be a Solid State Drive (SSD). The external memory 1034 may further include a flash drive, for example, Compact Flash (CF), Secure Digital (SD), Micro-Secure Digital (micro-SD), mini Secure Digital (mini-SD), eXtreme Digital (xD), or a memory stick. The external memory 1034 may be functionally connected to the electronic device 1000 through various interfaces. According to an embodiment of the present invention, the electronic device 1000 may further include a storage device (or storage medium) like a hard drive.

The sensor 1040, for example, the sensor 120 shown in FIG. 2, may measure a physical quantity of a physical property or detect an operating state of the electronic device 1000, and convert the measured or detected information into an electrical signal. The sensor 1040 may include at least one of, for example, a gesture sensor 1040A, gyro sensor 1040B, atmospheric pressure sensor 1040C, magnetic sensor, 1040D, acceleration sensor 1040E, grip sensor 1040F, proximity sensor 1040G, color sensor 1040H (e.g., a Red, Green, Blue (RGB) sensor), biometric sensor 1040I, temperature/humidity sensor 1040J or ambient light sensor 1040K, and Ultra Violet (UV) sensor 1040M. In addition to, or as an alternative to the above described elements of the sensor 1040, the sensor 1040 may include, for example, a e-nose sensor, an ElectroMyoGraphy (EMG) sensor, an ElectroEncephaloGram (EEG) sensor, an ElectroCardioGram (ECG) sensor, an Infra-Red (IR) sensor, an iris sensor, or a fingerprint sensor, etc. The sensor 1040 may further include a control circuit for controlling at least one sensor therein.

The input device 1050, for example, the input module 130 shown FIG. 2, may include a touch panel 1052, a (digital) pen sensor 1054, a key 1056, or an ultrasonic input device 1058. The touch panel 1052 recognizes a touch input in at least one of capacitive, pressure-sensitive, infra-red ray, and surface acoustic wave type. In addition, the touch panel 1052 may further include a control circuit (not shown). When the touch panel 1052 is capacitive type panel, physical contact or proximity recognition is possible. The touch panel 1052 may further include a tactile layer. In this case, the touch panel 1052 may provide a tactile reaction to the user.

The (digital) pen sensor 1054 may be implemented by using, for example, a method identical or similar to receiving user's touch input or a separate recognition sheet. The key 1056 may include, for example, physical buttons, or optical keys or a keypad. The ultrasonic input device 1058 may be a device able to detect a sound wave through a microphone and confirm data in the electronic device 1000 through an input tool generating an ultrasonic wave signal, and may be a device that enables wireless communication. According to an embodiment of the present invention, the electronic device 1000 may receive a user input from an external device (e.g., a computer or server) by using the communication module 1020.

The display 1060 (such as the output module 140 shown FIG. 2, for example) may include a panel 1062, a hologram device 1064 or a projector 1066. The panel 1062 may be, for example, a Liquid Crystal Display (LCD) or an Active-Matrix Organic Light-Emitting Diode (AMOLED). The panel 1062 may be implemented as, for example, a flexible, transparent or wearable panel. The panel 1062 may be configured as one module with the touch panel 1052. The hologram device 1064 shows a stereoscopic image in the air by using interference of lights. The projector 1066 displays an image by projecting a light on a screen. The screen may be located, for example, inside or outside the electronic device 1000. According to an embodiment of the present invention, the display 1060 may further include a control circuit for controlling the panel 1062, the hologram device 1064, or the projector 1066.

The interface 1070 may include, for example, a High-Definition Multimedia Interface (HDMI), 1072, a Universal Serial Bus (USB) 1074, an optical interface 1076 or a D-Subminiature (D-sub) 1078. Additionally or alternatively, the interface 1070 may include, for example, a Mobile High-definition Link (MHL) interface, a Secure Digital (SD) card/MultiMedia Card (MMC) interface, or an InfraRed Data Association (IrDA) specification interface.

The audio module 1080 converts sound into an electrical signal, or vice versa. The audio module 1080 processes sound information input from or output to, for example, a speaker 1082, receiver 1084, earphone 1086 or microphone 1088.

The camera module 1091 captures a still image or a video, and, according to an embodiment of the present invention, may include at least one image sensor (e.g., a front side sensor or a rear side sensor), a lens, an image signal processor (ISP), or a flash (e.g., an LED or xenon lamp).

The power management module 1095 manages power of the electronic device 200. Although not shown in the drawing, the power management module 1095 may include, for example, a Power Management Integrated Circuit (PMIC), a charger integrated circuit, or a battery or a fuel gauge.

The PMIC may be embedded, for example, in an IC or inside an SoC. A charging scheme may be either of a wireless and wired scheme. The charging IC may charge the battery and block inflow of over-voltage or over-current from a charger. According to an embodiment of the present invention, the charging IC may include a charging IC for at least one of a wired charging scheme or a wireless charging scheme. As the wireless charging scheme, for example, there is a magnetic resonance scheme, inductive coupling scheme, or microwave scheme. An additional circuit, for example, a coil loop, resonance circuit, or rectifier, etc., may be further included for wireless charging.

The battery gauge measures, for example, a remnant amount of the battery 1096, voltage, current or temperature while in charging. The battery 1096 stores or generates electricity and supplies power to the electronic device 1000 using the stored or generated electricity. The battery 1096 may include, for example, a rechargeable battery or solar battery.

The indicator 1097 displays a specific state of the electronic device 1000 or a portion thereof (e.g., the AP 1010), for example, a booting state, messaging state or charging state, etc. The motor 1098 converts an electrical signal into a mechanical vibration. Although not shown in the drawing, the electronic device 1000 may include a processing device (e.g., a GPU) for supporting a mobile TV. The processing device for supporting the mobile TV may process media data complying with specifications such as Digital Multimedia Broadcasting (DMB), Digital Video Broadcasting (DVB), or media flow, etc.

Each of the above-described elements according to various embodiments may be configured with one or more components, and a name of a corresponding element may vary according to a kind of electronic device. An electronic device according to various embodiments may be configured with at least one element among the above-described elements and some elements may be omitted or additional other elements may be further included. Furthermore, some of elements of an electronic device according to various embodiments may be combined to be one entity and perform the same functions as those of corresponding elements before the combination.

The term "module" used herein may mean, for example, a unit including a combination of one or two or more of hardware, software, or firmware. The "module" may be interchangeably used with a term, for example, a unit, logic, logical block, component, or circuit. A "module" may be a minimum or a portion of unit of a component configured into one. The "module" may be a minimum or a portion of unit performing one or more functions. A "module" may be implemented mechanically or electronically. For example, a "module" according to the specification may include at least one of an Application-Specific Integrated Circuit (ASIC) chip, Field-Programmable Gate Arrays (FPGAs), and programmable-logic devices that perform certain operations and are already known or to be developed.

According to various embodiments of the present invention, at least a portion of devices (e.g., modules or functions thereof) or methods (e.g., operations) according to various embodiments may be implemented as instructions stored in a computer-readable storage medium in the form of a programming module. When the instructions are performed by at least one processor, the at least one processor may perform functions corresponding to the instructions. The computer-readable storage medium may be, for example, a memory. At least a part of the programming module may be implemented (e.g., executed) by the processor. At least a part of the programming module may include, for example, a module, program, routine, sets of instructions, or process for performing at least one function.

The computer-readable storage medium may include a magnetic medium such as a hard disk, a floppy disk and a magnetic tape, an optical medium such as a Compact Disk Read Only Memory (CD-ROM) and a Digital Versatile Disc (DVD), a magneto-optical medium such as a floptical disk, and a hardware device configured to store and execute program instructions (e.g., programming module), such as a Read Only Memory (ROM), a Random Access Memory (RAM), and a flash memory. The program instructions may include machine language codes made by compilers and high-level language codes that can be executed by computers using interpreters. The above-mentioned hardware may be configured to be operated as one or more software modules for performing operations of various embodiments of the present invention and vice versa.

The module or programming module according to various embodiments of the present invention may include at least one of the above-mentioned elements, or some elements may be omitted or other additional elements may be added. Operations performed by the module, the programming module or the other elements may be performed in a sequential, parallel, iterative or heuristic way. Furthermore, some operations may be performed in another order or may be omitted, or other operations may be added.

An electronic device and method for providing external environment information according to various embodiments of the present invention can provide detailed environment information on an area in which the electronic device is located by using data obtained from at least one external electronic device that is able to communicate wirelessly and data measured by the electronic device.

Furthermore, an electronic device and method for providing external environment information according to various embodiments of the present invention can provide a history of changes in environment information according to the movement of the electronic device by using data obtained by the electronic device.

Furthermore, an electronic device and method for providing external environment information according to various embodiments of the present invention can easily provide environment information on a specific area on the basis of the location of the electronic device by creating a map representing environment information by using data obtained by the electronic device and data obtained by at least one external electronic device.

Furthermore, in an electronic device and method for providing external environment information according to various embodiments of the present invention, the electronic device located at a first location can provide environment information corresponding to a second location by receiving data obtained from external electronic devices located at the second location.

While certain embodiments of the present invention have been particularly shown and described above, it will be understood by one of ordinary skill in the art that various changes in form and details may be made therein without departing from the spirit and scope of the present invention as defined by the following claims and their equivalents. The above-described embodiments should be considered in a descriptive sense only and not provided for the purpose of limiting the scope of the invention. Therefore, the scope of the invention is defined not by the detailed description of embodiments but by the following claims and their equivalents, and all differences within the scope will be construed as being included in the present invention.

What is claimed is:

1. A mobile device comprising:
   a sensor configured to measure an environmental factor and obtain first data based on the measured environmental factor;
   a communication module configured to receive, from at least one external mobile device, second data obtained by the at least one external mobile device;
   a processor configured to generate environment information on an area in which the mobile device is located, calculated from the first data and the received second data; and
   an output module configured to display the environment information,
   wherein the first data, the second data and the environment information are associated with the same environmental factor including at least one of temperature, humidity, concentration of carbon dioxide, atmospheric pressure, and an ultraviolet index on the area in which the mobile device is located,
   wherein the mobile device requests second data from the at least one external mobile device through a provision server, and
   wherein the mobile device receives, from the provision server, at least one second data obtained by the at least one external mobile device.

2. The mobile device according to claim 1, wherein the at least one external mobile device is located within the area in which the mobile device is located.

3. The mobile device according to claim 1, wherein the generation of the environment information includes applying a respective weight or a respective priority to at least one of the first and second data.

4. The mobile device according to claim 3, wherein the processor checks a state of each of the mobile device and the at least one external mobile device based upon the first and second data and determines whether the weight or the priority is applied according to a result of checking the state of each of the mobile device and the at least one external mobile device.

5. The mobile device according to claim 1, wherein the first data includes a plurality of first data items obtained at a plurality of respective locations along a movement path of the mobile device,
   wherein the environment information includes a plurality of environment information items based on the plurality of first data items,
   wherein the processor is further configured to generate a history information map including the environment information, and
   wherein the output module is further configured to display the history information map.

6. The mobile device according to claim 1, wherein the processor is further configured to generate, when the first and second data are within a predetermined range each other,
   a group information map by grouping the first and second data together, and
   wherein the output module is further configured to display the group information map.

7. The mobile device according to claim 1, wherein the processor is further configured to check the second data obtained by the at least one external mobile device at a location corresponding to an input keyword and generate a movement route map including a route from a location a location of the mobile device to a location corresponding to the keyword, and
   wherein the output module is further configured to display the movement route map.

8. The mobile device according to claim 1, wherein the second data is generated based on an environmental factor measured by the at least one external mobile device.

9. A method of providing environment information, which is performed by a mobile device, the method comprising:
   measuring an environmental factor and obtaining first data based on the measured environmental factor;
   receiving, from at least one external mobile device, second data obtained by the at least one external mobile device;
   generating environment information on an area in which the mobile device is located, calculated from the first data and the received second data; and
   displaying the environment information,
   wherein the first data, the second data and the environment information are associated with the same environmental factor including at least one of temperature, humidity, concentration of carbon dioxide, atmospheric pressure, and an ultraviolet index on the area in which the mobile device is located,
   wherein the mobile device requests second data from the at least one external mobile device through a provision server, and
   wherein the mobile device receives, from the provision server, at least one second data obtained by the at least one external mobile device.

10. The method according to claim 9, wherein the at least one external mobile device is located within the area in which the mobile device is located.

11. The method according to claim 9, wherein generating the environment information includes applying a respective weight or a respective priority to at least one of the first and second data.

12. The method according to claim 11, further comprising:
   checking a state of each of the mobile device and the at least one external mobile device based upon the first and second data; and
   determining whether the weight or the priority is applied according to a result of checking the state of each of the mobile device and the at least one external mobile device.

13. The method according to claim 9, wherein measuring the environmental factor and obtaining the first data based on the environmental factor includes:
   obtaining a plurality of first data elements at a plurality of respective locations along a movement path of the mobile device,
   wherein generating the environment information includes generating a plurality of environment information items based on the plurality of first data items, and
   wherein the method further comprises:
   generating a history information map including the plurality of environmental information items; and
   displaying the history information map.

14. The method according to claim 9, further comprising:
   generating a group information map by grouping the first and second data when the first and second data are within a predetermined range each other; and
   displaying the group information map.

15. The method according to claim 9, further comprising:
generating a route map including a route from a location of the mobile device to a location corresponding to an input keyword and further including environment information of the location corresponding to the input keyword; and
displaying the route map.

16. The method according to claim 9, wherein the second data is generated based on an environmental factor measured by the at least one external mobile device.

17. A non-transitory computer readable storage medium having instructions recorded thereon, which, when executed by a computer, are able to control operations of a mobile device and allow the mobile device to perform a method comprising:
measuring an external environment and creating first data;
receiving second data from at least one external mobile device;
creating environment information on an area in which the mobile device is located, calculated from the first and second data; and
outputting the environment information,
wherein the first data, the second data and the environment information are associated with the same environmental factor including at least one of temperature, humidity, concentration of carbon dioxide, atmospheric pressure, and an ultraviolet index on the area in which the mobile device is located,
wherein the mobile device requests second data from the at least one external mobile device through a provision server, and
wherein the mobile device receives, from the provision server, at least one second data obtained by the at least one external mobile device.

* * * * *